United States Patent
Gibbons, Jr. et al.

(10) Patent No.: US 10,517,713 B2
(45) Date of Patent: Dec. 31, 2019

(54) VASCULAR GRAFT WITH HELICAL FLOW COMPLIANCE COMPARTMENTS

(71) Applicant: Cook Medical Technologies LLC, Bloomington, IN (US)

(72) Inventors: William S. Gibbons, Jr., Bloomington, IN (US); Kenneth A. Haselby, Battle Ground, IN (US); Jarin A. Kratzberg, Lafayette, IN (US); Keith R. Milner, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 37 days.

(21) Appl. No.: 15/867,483

(22) Filed: Jan. 10, 2018

(65) Prior Publication Data
US 2019/0209285 A1    Jul. 11, 2019

(51) Int. Cl.
*A61F 2/07* (2013.01)
*A61L 27/50* (2006.01)
*A61F 2/06* (2013.01)

(52) U.S. Cl.
CPC .......... *A61F 2/07* (2013.01); *A61F 2/06* (2013.01); *A61L 27/507* (2013.01);
(Continued)

(58) Field of Classification Search
None
See application file for complete search history.

(56) References Cited

U.S. PATENT DOCUMENTS 6,312,462 B1 * 11/2001 McDermott .............. A61F 2/07
                                                     623/1.25
6,395,019 B2    5/2002  Chobotov
(Continued)

FOREIGN PATENT DOCUMENTS

WO    WO 99/39662 A1    8/1999
WO    WO 01/66038 A2    9/2001
(Continued)

OTHER PUBLICATIONS

European Search Report for EP Application No. 19275002.4, dated May 23, 2019, 7 pages.
(Continued)

*Primary Examiner* — Megan Y Wolf
(74) *Attorney, Agent, or Firm* — Brinks Gilson & Lione

(57) ABSTRACT

A graft for inducing helical blood flow, including a tubular body with fluid inflow and fluid outflow ends, and with inner and outer sidewalls. A lumen extends between the fluid inflow end and fluid outflow end. A compressible chamber is disposed between the outer sidewall and the inner sidewall. The compressible chamber has an incompressible seam that follows a substantially helical path around a longitudinal axis of the tubular body. When internal (e.g., blood) pressure increases on the inner sidewall, a vane element is formed that follows the substantially helical path around the longitudinal axis of the tubular body. The vane element may induce helical blood flow. The width of the compressible chamber may decrease in a compressed state (e.g., systole). The chamber may be filled with a predetermined amount of at least one of a gas, liquid, or vapor. The graft may have a second incompressible seam/vane.

20 Claims, 3 Drawing Sheets

(52) U.S. Cl.
CPC . *A61F 2002/068* (2013.01); *A61F 2230/0091* (2013.01); *A61F 2250/0003* (2013.01); *A61F 2250/0018* (2013.01); *A61F 2250/0039* (2013.01)

(56) References Cited

U.S. PATENT DOCUMENTS

| | | |
|---|---|---|
| 7,682,673 B2 | 3/2010 | Houston et al. |
| 8,454,674 B2 | 6/2013 | Houston et al. |
| 8,454,675 B2 | 6/2013 | Houston et al. |
| 2006/0047334 A1* | 3/2006 | Houston ................. A61F 2/06 623/1.1 |
| 2007/0021707 A1 | 1/2007 | Caro et al. |
| 2010/0010518 A1* | 1/2010 | Stopek ................. A61B 17/11 606/153 |
| 2017/0007754 A1 | 1/2017 | Babbs et al. |
| 2017/0008854 A1 | 1/2017 | Babbs et al. |

FOREIGN PATENT DOCUMENTS

| | | |
|---|---|---|
| WO | WO 2004/060214 A1 | 7/2004 |
| WO | WO 2011/133019 A2 | 10/2011 |

OTHER PUBLICATIONS

European Search Report for EP Application No. 19275004.0, dated May 23, 2019, 8 pages.

\* cited by examiner

VASCULAR GRAFT WITH HELICAL FLOW COMPLIANCE COMPARTMENTS

BACKGROUND

Technical Field

This invention relates generally to medical devices and particularly to an endoluminal or subcutaneous graft for improving helical blood flow in a vessel.

Background

A primary physiological function of the aorta and its major branches is to convert the highly pulsative output of the left ventricle to a more nearly uniform and steady flow in the arterioles and capillaries, with minimum loss of energy. This requires that the peripheral vascular input impedance (which is a complex function of arterial resistance, fluid inertance, and arterial compliance) be matched to the output impedance of the heart.

Compliance is the ability of a vessel to distend and increase volume with increasing transmural pressure or to resist recoil towards its original dimensions on application of a distending or compressing force. Compliance can be defined as the fractional change in volume per change in pressure. In compliance, an increase in volume occurs in a vessel when the pressure in that vessel is increased. The tendency of the arteries and veins to stretch in response to pressure has a large effect on perfusion and blood pressure. Blood vessels with a higher compliance deform easier than lower compliance blood vessels under the same pressure and volume conditions. Veins have a much higher compliance than arteries (largely due to their thinner walls).

When a vessel loses compliance, it loses elasticity and typically becomes stiffer. Vessels, such as the aorta, can lose compliance due to age, congestive heart failure, atherosclerosis, etc. As the aorta stiffens and loses compliance, the heart struggles to pump blood and must work harder to eject the same volume of blood from the left ventricle into the aorta with each heartbeat. For example, a young person has a typical compliance of 6% dilation of the aorta with each heartbeat, whereas an older person with some arterial disease has a typical compliance of only 3%. If the heart is incapable of working harder because of underlying diseases, then less blood will be ejected into the aorta with each heartbeat.

A prostheses may be inserted into a body lumen such as an anatomical vessel or duct for various purposes. Prostheses may maintain or restore patency in a formerly blocked or constricted passageway or they may be used for different procedures, such as to facilitate dialysis.

Existing vascular grafts, including stent-grafts, covered stents, arterial bypass grafts, and arterio-venous grafts may be prone to stenosis or neointimal hyperplasia at the ends of the grafts, especially where the venous end of arterio-venous grafts are sutured to the vein. This occurrence has been attributed to a mismatch in the compliance of the graft compared to the vein. The graft may be substantially less compliant than the vein, which may lead to mechanical stresses on the vein and hemodynamic changes.

Additionally, literature has indicated that spiral laminar flow is the native flow regime in large arteries. "Recent work in cardiac and peripheral vascular blood flow has shown evidence for an elegant complexity to flow within the heart and in the large to medium arteries. Blood flow is normally described as laminar in that the blood travels smoothly or in regular paths. The velocity, pressure, and other flow properties at each point in the blood remain constant, all parallel to each other . . . . However, MRI and color Doppler flow imaging techniques have demonstrated that there is a spiral/helical/rotational property to laminar blood flow." Peter A. Stonebridge, "Three-Dimensional Blood Flow Dynamics: Spiral/Helical Laminar Flow," MDCVJ (2011).

For example, helical laminar flow has been shown within the aorta and may be a role in maintaining blood flow as the blood passes through the curved aortic arch. Similarly, helical laminar flow has been shown in peripheral and superficial arteries.

Helical flow may have a significant role within the aorta and other vessels. For example, it may have a positive role in the transportation of oxygen to the vessel wall. It may also increase wall shear stress, which results in fewer instances of thrombosis, turbulence, stenosis, and neointimal hyperplasia.

Endoluminal prostheses may be inserted into a body lumen such as an anatomical vessel or duct for various purposes. Prostheses may maintain or restore patency in a formerly blocked or constricted passageway or they may be used for different procedures, such as to facilitate dialysis.

Existing vascular grafts, including stent-grafts, covered stents, arterial bypass grafts, and arterio-venous grafts may be prone to stenosis or neointimal hyperplasia at the distal anastomosis, which eventually can occlude outflow.

It is therefore desirable to have a device configured to induce helical blood flow. As a result, there may be reduced thrombosis within the graft and reduced neointimal hyperplasia and stenosis on the distal end of the graft where it transitions to the blood vessel.

SUMMARY OF INVENTION

A graft for inducing helical blood flow having a tubular body with a fluid inflow end, a fluid outflow end, an outer sidewall, an inner sidewall, a lumen extending between the fluid inflow end and fluid outflow end, and a compressible chamber between at least a portion of the outer sidewall and the inner sidewall. The compressible chamber may have a first incompressible seam that follows a first substantially helical path around a first longitudinal axis of the tubular body, and in response to internal pressure on the inner sidewall a first vane element may be formed that follows the substantially helical path around the first longitudinal axis of the tubular body.

The outer sidewall and inner sidewall of the graft may extend from the fluid inflow end to the fluid outflow end. The chamber may be filled with a predetermined amount of at least one of a gas, liquid, or vapor. The gas may be carbon dioxide. The chamber may have a port constructed and dimensioned to receive a fluid, vapor, or gas during a filling state.

The chamber may extend from the fluid inflow end of the graft to the fluid outflow end of the graft. The helical path may be either right-handed or left-handed. The first incompressible seam may extend from the fluid inflow end of the graft to the fluid outflow end of the graft.

The compressible chamber may further include a second incompressible seam that follows a second substantially helical path around a second longitudinal axis of the tubular body, and in response to internal pressure on the inner sidewall a second vane element may be formed that follows the second helical path around the second longitudinal axis of the tubular body.

The compressible chamber may have a chamber width between the outer sidewall and the inner sidewall. The chamber may be constructed and dimensioned such that in a nominal state the chamber has a nominal chamber width and such that in a compressed state the chamber has a compressed chamber width less than the nominal chamber width. The chamber may have a nominal state during diastole and a compressed state during systole. The first vane element may induce helical fluid flow through the lumen during systole.

The graft may further include at least one stent. The first helical path may have a helical angle between 15° and 50°. The tubular body may be made of one of the following materials: PET, nylon, ePTFE, and Dacron. The chamber may have at least one helical turn, or in another example, at least two helical turns.

The graft may be constructed and dimensioned to change from a delivery configuration to a deployment configuration during a deployment step. The may have a reduced diameter during the delivery configuration and an expanded diameter during the deployment configuration.

DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like reference numerals designate corresponding parts throughout the different views.

DETAILED DESCRIPTION

As used here, the term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device, respectively. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the delivery device and the distal end of the prosthesis is that end that is closest to the operator end of the delivery device. When referring to the prosthesis relative to placement in the human body, the ends of the various devices and parts of devices may be referred to as the proximal end or fluid inflow end (that end that receives blood first), and the distal end or fluid outflow end (that end from which the blood exits). When used herein, the term "compliance" is referred to as the fractional change in volume per unit change in pressure.

The present disclosure relates to the subject matter of U.S. application Ser. No. 14/791,712, filed Jul. 6, 2015, published as US 2017/0007754 A1, and entitled "Endovascular Compliance Assembly," the entirety of which is incorporated by reference herein in its entirety.

Grafts of the present invention may be placed endoluminally. A graft may also be placed subcutaneously or surgically. With dialysis access grafts, grafts in the patient forearm or upper arm are placed surgically by suturing one end of the graft to an end or side of an artery, suturing the other end of the graft to an end or side of a vein, while the remainder of the graft is placed subcutaneously in the forearm or upper arm (i.e. the graft is placed subcutaneously and not within the lumen of another vessel.

Figure 1:
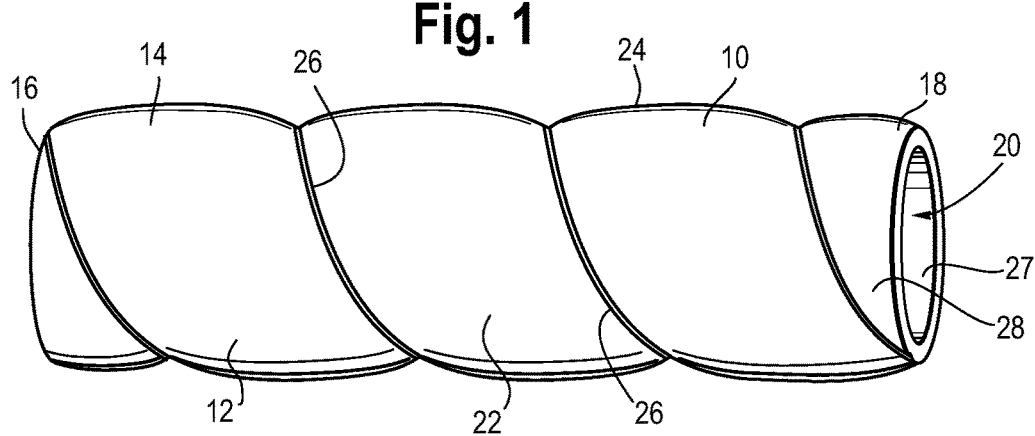
FIG. 1 depicts an embodiment of an endoluminal graft.

FIG. 1 depicts an embodiment of an endoluminal graft 10. In one example, the graft 10 shown in FIGS. 1-6 may be sutured into a blood vessel. Although the graft 10 can be independent as represented in FIGS. 1-6, the graft 10 as described below may also be incorporated into new or existing vascular grafts, including stent-grafts, covered stents, arterial bypass grafts, and arterio-venous grafts.

As shown in FIG. 1, a tubular conduit, namely a vascular graft 10 that may be in the shape of a flexible hollow cylindrical tube. The graft 10 may comprise a tubular body 12 of biocompatible graft material 14 having a proximal end 16 (fluid inflow end) and a distal end 18 (fluid outflow end) and a main lumen 20 extending therethrough.

The graft 10 may have one or more compliance chambers 22 within a sidewall 24 of the tubular body 12. The sidewall 24 may have an inner wall 27 and an outer wall 28. As shown in FIG. 1, the compliance chamber 22 may be comprised of an inflatable helical-cylindrical chamber formed within the sidewall 24 of the tubular body 12. In one example, the compliance chamber 22 is formed between the inner wall 27 and the outer wall 28. The helical compliance chamber 22 may extend from the proximal end 16 to the distal end 18 of the graft 10. In another example (not shown), the helical compliance chamber 22 may only extend partially along the length of graft 10.

The helical compliance chamber 22 may have an open channel therethrough. The open channel may contain the main lumen 20 that extends through the graft 10.

In one example (shown in FIG. 1), the helical compliance chamber 22 may be wrapped or encapsulated within a sidewall 24 of the graft 10. In other words, the helical compliance chamber 22 may be embedded within the graft material 14 between the inner wall 27 and the outer wall 28. For example, the helical compliance chamber 22 may be encapsulated, sandwiched, or incorporated between sheets of graft material 14 that make up the sidewall 24 of the tubular body 12.

A seam 26 may extend along the length of the graft 10 in a helical configuration between the edges 28 of the helical compliance chamber 22. The seam 26 may make one or more helical turns along the length of the graft. The seam 26 may follow a substantially helical path 34 (see FIG. 5) around a central longitudinal axis of the tubular body.

The seam 26 may be incompressible, such that in response to internal pressure (e.g., increased blood pressure) on the inner wall a helical vane element may form within the lumen 20. The helical vane element may induce helical fluid flow within the lumen 20 and/or in the endoluminal space distal to the distal end 18 (outflow end) of the graft 10. The vane element may induce helical fluid flow by directly protruding into and impinging on the blood stream to deflect the blood and cause helical flow.

The helical compliance chamber 22 may have a helical path 34 (see FIG. 5) by virtue of the helical seam 26. The helical path 34 may be either right-handed or left-handed. Handedness (or chirality) is a property of the helix, not of the perspective. For example, with the line of sight along a helix's axis, if a clockwise screwing motion moves the helix away from the observer, then it is called a right-handed helix; if towards the observer, then it is a left-handed helix. The helical compliance chamber 22 may have a central longitudinal axis, for example, the central longitudinal axis of the tubular body, or an off-center longitudinal axis. The helical compliance chamber 22 may have a helix angle. The helix angle can be found by unraveling the helix from the compliance chamber 22, representing the section as a right triangle, and calculating the angle that is formed. In one example, the helix angle is between 15 and 50 degrees) (15-50°).

The compliance chamber 22 may be constructed using any known technique. In one example, two or more layers of graft material 14 may be adhered together to form one or more chambers. For example, two tubes of graft material may be concentrically adhered to each other. In another example, the layers of graft material may be heat-set to form the chamber 22. In another example, a balloon may be bonded between the layers of graft material 14.

In one example (shown in FIG. 1), the helical compliance chamber 22 is incorporated into the tubular body 12 of the graft 10 and extends axially along the length of the tubular body. The chamber 22 may be enclosed within the sidewall 24 of the graft material 14, for example, between the sheets of graft material 14 that comprise the sidewall 24 (e.g., inner wall 27 and the outer wall 28). The incompressible seam 26 may be created by differences in compliance (rigidity) between the graft material 14 of the inner wall 27 and outer wall 28 (including seam 26). The graft material 14 of the outer wall 28 and seam 26 may be less compliant (more rigid) than the graft material 14 of the inner wall 27. As a result, when the pressure in the lumen 20 increases (e.g., during systole), the inner wall 27 is compressed towards the outer wall 28 while the less compliant (more rigid) incompressible seam 26 remains in place. By remaining in place relative to the inner wall 27, the seam 26 protrudes into the lumen 20 and forms a helical vane. As used herein, the term "incompressible" means generally incompressible relative to the compliance chamber 22. It is understood that the seam 26 may compress slightly under pressure, but it may be referred to as "incompressible" so long as it compresses substantially less than the inner wall 27 such that it forms the helical vane.

In an alternative example (not shown), the incompressible seam 26 may form a helical groove through the compliance chamber, such that instead of protruding into the lumen 20, the groove is recessed from the lumen 20. In such an example, the helical compliance chamber 22 may have sufficient volume during the compressed state such that the groove (seam 26) has an adequate depth and is not flush with the inner wall 27. The depth should be adequate so as to induce helical flow through the lumen 20.

The helical compliance chamber 22 may be made of the same biocompatible material as the graft material 14 (described in greater detail below), or the helical chamber 22 may be made of any other biocompatible material. In one example the helical compliance chamber 22 is made out of nylon or polyester.

Helical compliance chamber 22 may be at least partially filled with any suitable fluid, including a gas, liquid, or vapor. For example, suitable gas may include carbon dioxide. Suitable vapors may include ethyl alcohol or dimethyl ether.

Suitable liquids might include saline. The amount of gas, liquid, or vapor may be predetermined.

Compliance chamber 22 may be inflated or filled to a particular volume or a particular pressure. In one example, the compliance chamber 22 is filled after the graft 10 has been delivered to the target site. In one example, the compliance chamber 22 may be filled using one or more ports (not shown) in compliance chamber 22 during a filling state or step. The filling state or step may be before the graft 10 has been delivered to the target site.

The compressibility of the helical compliance chamber 22 can be adjusted by selection of dimensions, manufacturing materials, volume of gas and/or vapor and/or liquid inside the chamber, and/or choice of gas, vapor, or liquid within the chamber in order to create the desired compliance. For example, the volume and mixture of the gas, liquid, or vapor selected to at least partially fill the compliance chamber 22 may be chosen so that the compliance chamber 22 would be compressed during systole because of the increased blood pressure, resulting in the formation of a helical vane within the lumen 20 due to the incompressible seam 26, and an increase in the compliance of the graft 10 compared to a standard graft.

The graft 10 and helical compliance chamber 22 may be any suitable selected diameter and may be constructed with any biocompatible graft material 14. The graft material 14 may be synthetic and/or naturally-derived material. Synthetic biocompatible polymers may include but are not limited to polyethylene terephthalate, polyurethane, nylon, polyester, high molecular weight polyethylene (such as Thoralon), polytetrafluoroethylene, or combinations thereof. The graft material 14 can be porous or non-porous and also may be impregnated or coated with one or more therapeutic substances. In one example, the graft material 14 may be constructed of the commercially available material referred to as PET, nylon, ePTFE, or Dacron. The graft material 14 should have sufficient flexibility to allow for navigation of the vasculature and delivery to a targeted area in the body. Preferably, the graft material 14 is a low profile material or an ultralow profile material.

The graft 10 may be any length, width, and diameter. Similarly, the helical compliance chamber 22 may be any length, width, and diameter. In one example, the graft 10 is between 25-35 mm in diameter and 10-40 cm length. In one example, the compliance chamber 22 is between 100-200 cc in volume. With the exception of the seam 26, the compliance chamber 22 may be of uniform size, or alternatively, may vary along the length of the graft 10. The compliance chamber 22 may have a compliance between 1% and 50%. The compliance chamber 22 may have a compliance of 3% to 30%.

The graft 10 may be expandable from a smaller diameter to a larger diameter. The graft 10 may be delivered to the deployment site in a delivery configuration (not shown), and once located and oriented at the deployment site the graft may expand to a deployment configuration.

The graft 10 may be delivered using any known delivery method, including minimally invasive techniques. In one example, the graft 10 can be inserted using a minimally invasive technique such as through a delivery catheter. Graft 10 could also be sewn into a vessel, duct, or lumen during an open procedure. Any known anchoring means may be provided with the graft 10 to prevent migration of the graft 10 in a vessel, duct, or lumen. In one example, a stent (not shown) with one or more anchoring barbs may be attached to graft 10.

Figure 2:
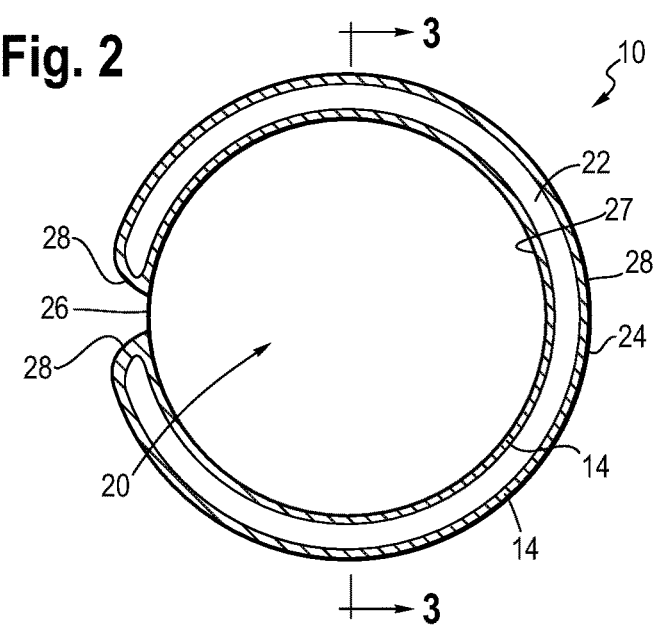
FIG. 2 depicts a transverse cross-sectional view of the endoluminal graft shown in FIG. 1 in a nominal state, for example, during diastole.

FIG. 2 depicts a transverse cross-sectional view of the endoluminal graft shown in FIG. 1 during diastole. As shown in FIG. 2, the helical compliance chamber 22 is within the sidewall 24 of the graft 10. In one example, the helical compliance chamber 22 is sandwiched or embedded between two layers of graft material 14 that form the inner wall 27 and outer wall 28 of the sidewall 24. In between the edges of outer wall 28 of the helical compliance chamber 22 there may be an incompressible seam 26. The incompressible seam 26 may follow a substantially helical path 34 around a central longitudinal axis of the tubular body.

As previously discussed, the helical compliance chamber 22 may be partially or fully filled with a gas, liquid, or vapor. The helical compliance chamber 22 may be any thickness or width, as measured as the distance between the outer sidewall 28 and the inner sidewall 27. The transverse cross-section of the helical compliance chamber 22 may essentially form a partial annulus (region lying between two concentric circles) due to the seam 26 and/or vane element. The thickness or width of the compliance chamber 22 is the width of the partial annulus. The helical compliance chamber 22 may be constructed and dimensioned such that in a nominal state the chamber 22 has a nominal chamber width, and such that in a compressed state the chamber 22 has a compressed chamber width less than the nominal chamber width.

The helical compliance chamber 22 may be constructed and dimensioned to retain its nominal state (and nominal width) during diastole (but, as will be described below in FIG. 4, it may be compressed to a compressed state with a compressed width, less than the nominal width, during systole when the blood pressure increases). A main lumen 20 may extend through the center of graft 10.

The diameter and cross-sectional shape of the graft 10 allows for blood to flow in a proximal to distal direction through the lumen 20.

Figure 3:
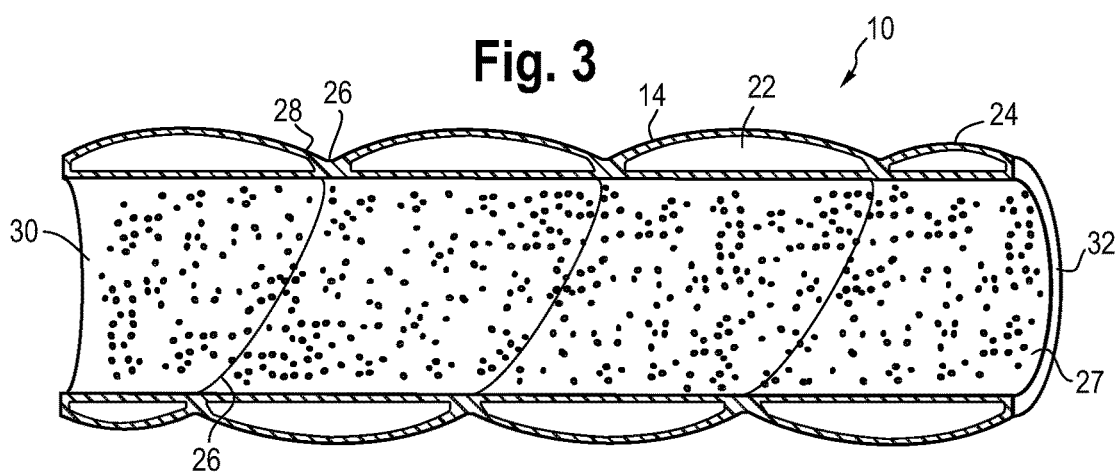
FIG. 3 depicts a longitudinal cross-sectional view of the graft of FIG. 1 in a nominal state, for example, during diastole.

FIG. 3 depicts a longitudinal cross-sectional view of the graft of FIG. 1 during diastole. The dots within lumen 20 indicate blood. As shown, during diastole the helical compliance chamber 22 may be in a nominal state and have a nominal width. The incompressible seam 26 may be flush with the inner wall 27 and thus not impinge on the blood flow. The lumen 20 of the graft 10 may be configured to receive a blood flow. In one example, blood may flow into the proximal or inflow end 30 of the graft 10 and may exit the graft at the distal or outflow end 32. During diastole, blood pressure may be nominal so the blood may fill substantially uniformly through the lumen 20 of the graft 10.

Figure 4:
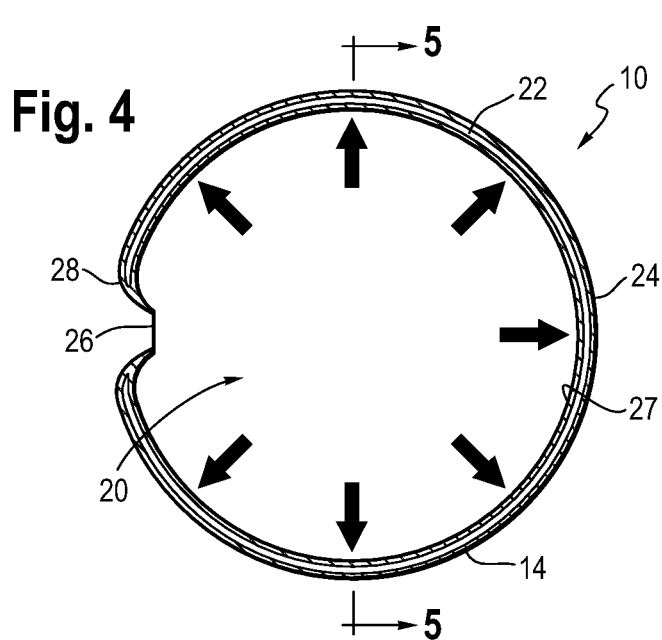
FIG. 4 depicts a transverse cross-sectional view of the endoluminal graft shown in FIG. 1 in a compressed state, for example, during systole.

FIG. 4 depicts a transverse cross-sectional view of the endoluminal graft shown in FIG. 1 during systole. As shown in FIG. 4, during systole the blood pressure forces apply pressure from the lumen 20 to the interior of the graft sidewall 24 (e.g., inner wall 27). During systole, there is higher pressure in the aorta. Blood flow forces may increase causing the helical compliance chamber 22 to compress to a compressed state. In the compressed state (systole), the chamber 22 may have a compressed width that is less than the nominal chamber width during the nominal state (diastole). As shown in FIG. 4, the width of the helical compliance chamber 22 in the compressed state (systole) is less than the nominal width of the helical compliance chamber 22 shown in FIG. 2 (nominal state, diastole).

The seam 26 may be incompressible between the edges 28 of the helical compliance chamber 22. In response to internal pressure (e.g., increased blood pressure) on the inner wall during systole, the seam 26 may form a vane element, thereby inducing helical blood flow along the graft by directly protruding into and impinging on the blood stream to deflect the blood and cause helical flow. During the systolic cycle, the compressed helical compliance chamber 22 may take on a geometry inducing helical blood flow.

Figure 5:
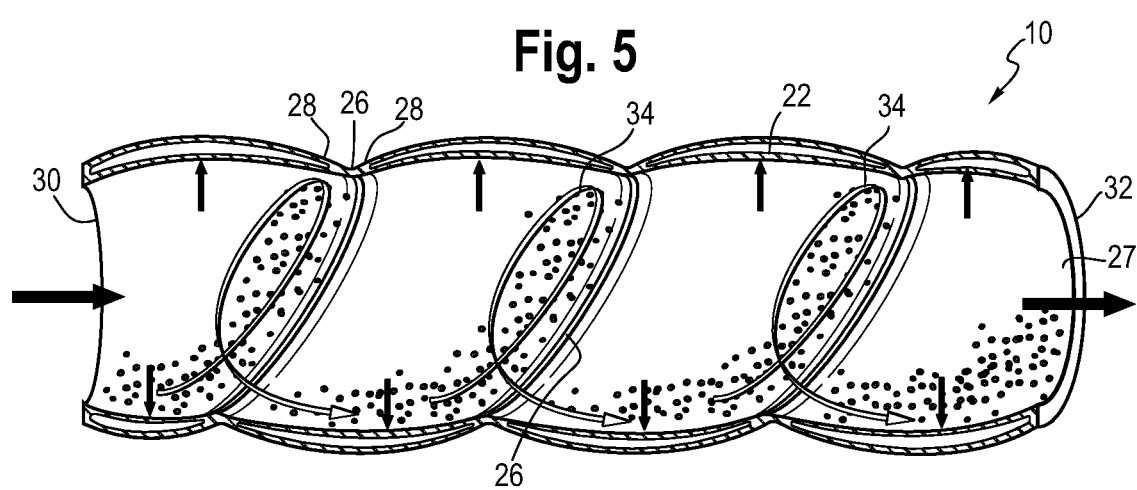
FIG. 5 depicts a longitudinal cross-sectional view of the graft of FIG. 1 in a compressed state, for example, during systole.

FIG. 5 depicts a longitudinal cross-sectional view of the graft of FIG. 1 during systole. As described above, during the systolic cycle, the compressed helical compliance chamber 22 may receive increased internal pressure (e.g., increased blood pressure) on the inner wall 27. The incompressible seam 26 is incompressible along the edges 28 of the outer wall of the compliance chamber 22. Thus, the incompressible seam 26 may form a vane element inducing helical blood flow by virtue of the vane element impinging on blood flow within the lumen 20. The result is that blood flow will flow in a helical path 34 near the seam 26 of the helical compliance chamber 22. Blood flowing in a helical path 34 near the vane element caused by seam 26 may induce a helical flow in the surrounding blood flow throughout the lumen 20 and in blood vessels distal to the graft 10.

As shown in FIG. 5, blood flow will enter the graft 10 in the fluid inflow end 30 and exit the graft 10 at the fluid outflow end 32. The blood may take a helical path 34 as it travels from the fluid inflow end 30 to the fluid outflow end 32. The helical path 34 may significantly follow the path of the seam 26 in a helical pattern.

Figure 6:
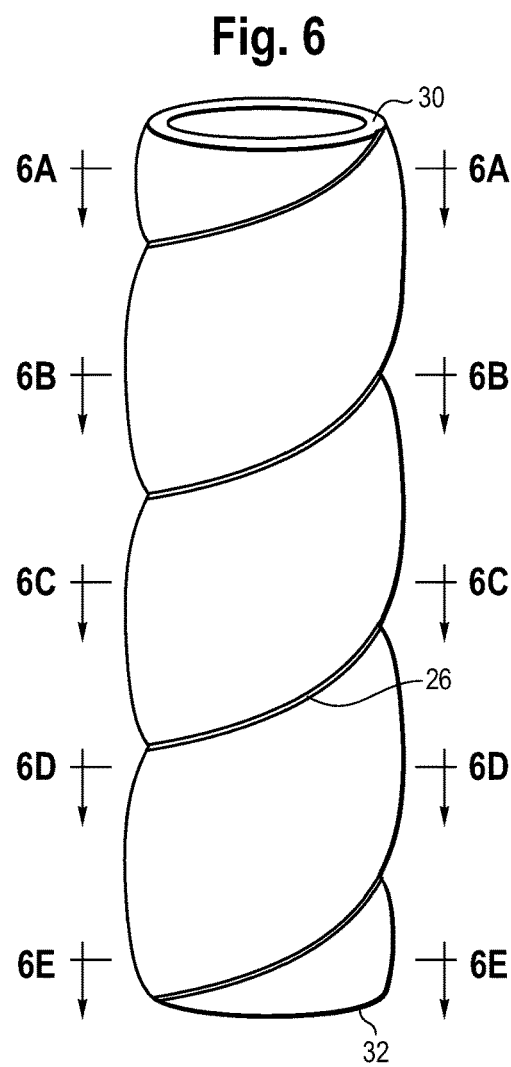
FIG. 6 depicts an embodiment of an endoluminal graft in a compressed state, for example, during systole.
Figure 6A:
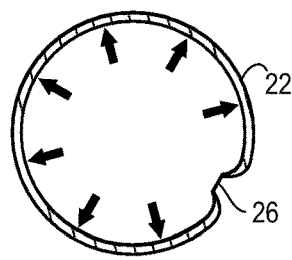
FIG. 6A depicts a transverse cross-sectional view of the endoluminal graft in the compressed state shown in FIG. 6, along the line 6A shown in FIG. 6.
Figure 6B:
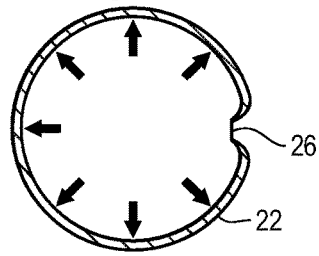
FIG. 6B depicts a transverse cross-sectional view of the endoluminal graft in the compressed state shown in FIG. 6, along the line 6B shown in FIG. 6.
Figure 6C:
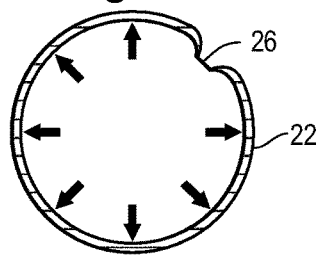
FIG. 6C depicts a transverse cross-sectional view of the endoluminal graft in the compressed state shown in FIG. 6, along the line 6C shown in FIG. 6.
Figure 6D:
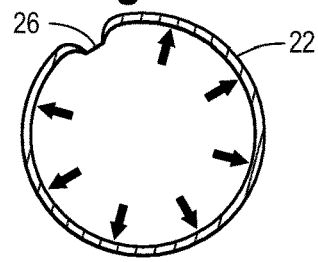
FIG. 6D depicts a transverse cross-sectional view of the endoluminal graft in the compressed state shown in FIG. 6, along the line 6D shown in FIG. 6.
Figure 6E:
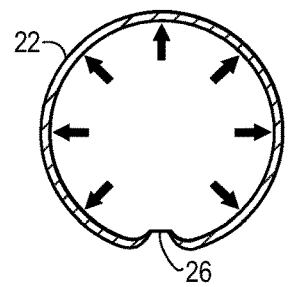
FIG. 6E depicts a transverse cross-sectional view of the endoluminal graft in the compressed state shown in FIG. 6, along the line 6E shown in FIG. 6.

FIG. 6 depicts an embodiment of an endoluminal graft in a compressed state, for example, during systole. FIG. 6A depicts a transverse cross-sectional view of the endoluminal graft in the compressed state shown in FIG. 6, along the line 6A shown in FIG. 6. FIG. 6B depicts a transverse cross-sectional view of the endoluminal graft in the compressed state shown in FIG. 6, along the line 6B shown in FIG. 6. FIG. 6C depicts a transverse cross-sectional view of the endoluminal graft in the compressed state shown in FIG. 6, along the line 6C shown in FIG. 6. FIG. 6D depicts a transverse cross-sectional view of the endoluminal graft in the compressed state shown in FIG. 6, along the line 6D shown in FIG. 6. FIG. 6E depicts a transverse cross-sectional view of the endoluminal graft in the compressed state shown in FIG. 6, along the line 6E shown in FIG. 6.

FIGS. 6 and 6A-6E show the blood pressure (radially outward arrows) on the internal wall of the graft as the blood flows through the graft 10. As blood flows from the fluid inflow end 30 to the fluid outflow end 32, the blood pressure forces apply pressure on the inner wall 27 of the graft 10 and helical compliance chamber 22. The seam 26 between the edges of outer wall 28 of the helical compliance chamber 22 does not compress like the helical compliance chambers 22.

As shown in FIGS. 6A-6E, the blood pressure exerts radially outward forces on compressible part of the graft (the chamber 22) as blood flows from the fluid inflow end 30 to the fluid outflow end 32. As a result, the seam 26 forms a vane element that follows the substantially helical path 34 around the longitudinal axis of the tubular body. The vane element directly impinges on the blood flow to deflect the blood and induce a helical fluid flow.

The graft 10 disclosed induces helical blood flow within the lumen 20 of the graft 10 during systole. The helical flow may persist after systole so long as the blood continues to move. The helical flow may also persist after the blood leaves the distal outflow end 18 of the graft 10. As a result, there may be (1) reduced turbulence within the blood vessel; (2) reduced wall pressures and stresses; (3) reduced particle adhesion to the vessel wall—the particles are held in the center of the vessel; and (4) improved blood flow through stenosis or blockages.

In another example (not shown), the compressible chamber 22 may further comprises a second incompressible seam that follows a second substantially helical path around a second longitudinal axis of the tubular body. The second longitudinal axis may be the same as the first longitudinal axis. Like the first vane element, a second vane element may be formed in response to increased internal pressure on the inner sidewall. The second vane element may follow the second helical path around the second longitudinal axis of the tubular body. The second vane element may further facilitate the inducement of helical blood flow within the lumen 20 of the graft 10 and beyond. Likewise, additional seams/vanes may be added as appropriate.

While preferred embodiments of the invention have been described, it should be understood that the invention is not so limited, and modifications may be made without departing from the invention. Moreover, the advantages described herein are not necessarily the only advantages of the invention and it is not necessarily expected that every embodiment of the invention will achieve all of the advantages described.

We claim:

1. A graft for inducing helical blood flow, the graft comprising:
   a tubular body having a fluid inflow end and a fluid outflow end, the tubular body having an outer sidewall and an inner sidewall;
   a lumen extending between the fluid inflow end and fluid outflow end; and
   a compressible chamber disposed between at least a portion of the outer sidewall and the inner sidewall, wherein the compressible chamber has a first incompressible seam that follows a first substantially helical path around a first longitudinal axis of the tubular body,
   wherein in response to internal pressure on the inner sidewall during systole the first incompressible seam protrudes within the lumen forming a first helical vane element that follows the first substantially helical path.

2. The graft of claim 1, wherein the outer sidewall and inner sidewall extend from the fluid inflow end to the fluid outflow end.

3. The graft of claim 1, wherein the compressible chamber is filled with a predetermined amount of at least one of a gas, liquid, or vapor.

4. The graft of claim 3, wherein the gas is carbon dioxide.

5. The graft of claim 1, wherein the compressible chamber extends from the fluid inflow end of the graft to the fluid outflow end of the graft.

6. The graft of claim 1, wherein the first substantially helical path is either right-handed or left-handed.

7. The graft of claim 1, wherein the compressible chamber further comprises a second incompressible seam that follows a second substantially helical path around a second longitudinal axis of the tubular body,
   wherein in response to internal pressure on the inner sidewall a second vane element is formed that follows the second substantially helical path.

8. The graft of claim 1, wherein the compressible chamber has a chamber width between the outer sidewall and the inner sidewall, and the compressible chamber is constructed and dimensioned such that in a nominal state the compressible chamber has a nominal chamber width and such that in a compressed state the compressible chamber has a compressed chamber width less than the nominal chamber width.

9. The graft of claim 8, wherein the compressible chamber has the nominal state during diastole and has the compressed state during systole.

10. The graft of claim 1, further including at least one stent.

11. The graft of claim 1, wherein the first substantially helical path has a helical angle between 15 degrees and 50 degrees.

12. The graft of claim 1, where the tubular body is made of one of the following materials: PET, nylon, ePTFE, and Dacron.

13. The graft of claim 1, wherein the compressible chamber has at least one helical turn.

14. The graft of claim 1, wherein the compressible chamber has at least two helical turns.

15. The graft of claim 1, wherein the graft is constructed and dimensioned to change from a delivery configuration to a deployment configuration during a deployment step.

16. The graft of claim 15, wherein the graft has a reduced diameter during the delivery configuration and an expanded diameter during the deployment configuration.

17. The graft of claim 1, wherein the compressible chamber has a port constructed and dimensioned to receive a fluid, vapor, or gas during a filling state.

18. The graft of claim 1, wherein the first incompressible seam extends from the fluid inflow end of the graft to the fluid outflow end of the graft.

19. The graft of claim 1, wherein the first helical vane element induces helical fluid flow through the lumen during systole.

20. A method for inducing helical blood flow in a vessel, the method comprising:
   delivering a graft to a target site, the graft comprising: a tubular body having a fluid inflow end and a fluid outflow end, the tubular body having an outer sidewall and an inner sidewall; a lumen extending between the fluid inflow end and fluid outflow end; and a compressible chamber disposed between at least a portion of the outer sidewall and the inner sidewall, wherein the compressible chamber has an incompressible seam that follows a substantially helical path around a first longitudinal axis of the tubular body; and
   at least partially filling the compressible chamber with a fluid, vapor, or gas so that in response to internal pressure on the inner sidewall during systole the incompressible seam protrudes within the lumen forming vane element inducing helical fluid flow.

* * * * *